United States Patent
Hayden (10) Patent No.: US 7,803,158 B2
(45) Date of Patent: Sep. 28, 2010

(54) NAVIGATED PIN PLACEMENT FOR ORTHOPAEDIC PROCEDURES

(75) Inventor: Adam Iredell Hayden, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1067 days.

(21) Appl. No.: 10/811,338

(22) Filed: Mar. 26, 2004

(65) Prior Publication Data

US 2005/0216032 A1 Sep. 29, 2005

(51) Int. Cl.
*A61B 17/56* (2006.01)
*A61B 17/88* (2006.01)
*A61B 17/90* (2006.01)

(52) U.S. Cl. .................. 606/80; 606/86 R; 606/87; 606/88; 606/89; 606/96; 606/98

(58) Field of Classification Search ............ 606/79, 606/86–89, 96–98, 86 R
See application file for complete search history.

(56) References Cited

U.S. PATENT DOCUMENTS

| | | | | |
|---|---|---|---|---|
| 4,365,624 A | * | 12/1982 | Jaquet | 606/56 |
| 4,952,213 A | * | 8/1990 | Bowman et al. | 606/79 |
| 5,228,459 A | * | 7/1993 | Caspari et al. | 128/898 |
| 5,514,143 A | * | 5/1996 | Bonutti et al. | 606/86 |
| 5,601,551 A | * | 2/1997 | Taylor et al. | 606/54 |
| 5,688,279 A | | 11/1997 | McNulty et al. | |
| 6,056,748 A | * | 5/2000 | Weiner | 606/55 |
| 6,090,114 A | * | 7/2000 | Matsuno et al. | 606/88 |
| 6,168,628 B1 | * | 1/2001 | Huebner | 623/19.11 |
| 6,697,664 B2 | | 2/2004 | Kienzle, III et al. | |
| 2002/0198531 A1 | | 12/2002 | Millard et al. | |
| 2003/0060703 A1 | | 3/2003 | Barrick | |
| 2004/0039396 A1 | | 2/2004 | Couture et al. | |
| 2005/0020909 A1 | | 1/2005 | Moctezuma et al. | |

FOREIGN PATENT DOCUMENTS

| | | |
|---|---|---|
| EP | 1 302 167 | 4/2003 |
| WO | WO02/064042 | 8/2002 |
| WO | WO03/043485 | 5/2003 |
| WO | WO03/096920 | 11/2003 |

* cited by examiner

*Primary Examiner*—Thomas C Barrett
*Assistant Examiner*—Sameh Boles
(74) *Attorney, Agent, or Firm*—Maginot, Moore & Beck (57) ABSTRACT

Systems and methods are provided for navigated placement of bone engaging elements, such as support pins used to support a cutting block on a bone for resection. In one embodiment, a guide apparatus is configured to be mounted to a bone and provides multi-degree of freedom gross and fine adjustments of a pin guide. The pin guide carries a position tracking element so that its real-time spatial position relative to a location on the bone can be evaluated.

20 Claims, 4 Drawing Sheets

NAVIGATED PIN PLACEMENT FOR ORTHOPAEDIC PROCEDURES

BACKGROUND OF THE INVENTION

The present invention relates to systems and methods for accurate positioning of tools, fasteners and implants within a patient. More particularly, the invention relates to orthopaedic surgical procedures requiring accurate shaping of the bone or placement of bone engaging elements.

Damage or disease can deteriorate the bones, articular cartilage and ligaments of human joints, such as the knee, which can ultimately affect the ability of the natural joint to function properly. To address these conditions, prosthetic joints have been developed that are mounted to prepared ends of the bones of the joint, namely the tibia and femur in the case of a knee prosthesis.

The implant components define interior mounting surfaces that often require involved cuts into the bone, such as the distal end of the femur or the proximal end of the tibia. The implant components are selected to restore or emulate as much of the natural motion of the knee joint as possible. Consequently, implant positioning with respect to the natural bone is critical. For instance, a proper implant will maintain the proper tension in the retained ligaments supporting the joint.

Figure 1:
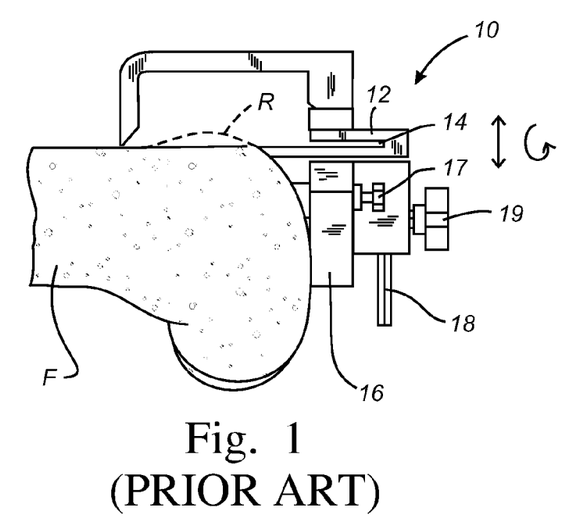
FIG. 1 is a side view of an adjustable cutting block mounted to the distal end of a femur.

Preparation of the natural joint to receive a prosthesis must be painstaking to ensure the properly selected implant will work for its intended purpose. For instance, in preparing a knee joint to receive a prosthesis, the orthopaedic surgeon typically uses templates to determine the proper size of the implant components. The surgeon may also measure the joint gap and choose a spacer that can be used in the procedure to maintain that gap. Since the femoral component of the knee prosthesis requires complex cuts in the femur, a femoral resection guide is used, such as the resection guide 10 shown in FIG. 1. A saw guide 12 is aligned with the end of the femur F with its guide slot 14 oriented to make the proper cut in the bone. The saw guide is supported on the bone by a mounting block 16 that is fastened to the distal end of the femur F by a pair of mounting pins 17. The orientation of the saw guide 12 is adjusted by controlling an adjustment knob 19 and sliding an adjustment rod 18.

While the vertical position of the saw guide slot 14 is adjusted by sliding the adjustment rod 18 relative to the mounting block 16, the angular orientation of the saw guide is determined by the placement of the mounting pins 17 supporting the mounting block. It can be appreciated, then, that the placement of the mounting pins 17 must be as accurate as possible to ensure a proper cut. In order to account for the potential for error in initial placement of the pins, more complex cutting guide assemblies have been developed. These complex devices include multiple degree-of-freedom fine tuning adjustments that can be "dialed in" to optimize the orientation of the saw guide. While accurate bone cuts can be made with these complex devices, they are naturally more expensive and require greater maintenance than cutting blocks as simple as or more simple than the assembly 10 of FIG. 1.

Many orthopaedic procedures require performing operations on only partially exposed bones and joints. The use of an imaging modality such as intraoperative x-rays or CT scans can open the surgeon's "field of vision" without requiring greater tissue exposure of the patient. Image guided surgical techniques have been used in orthopaedic surgeries, as well as many other types of surgeries where the surgical site is difficult to view directly.

Figure 2:
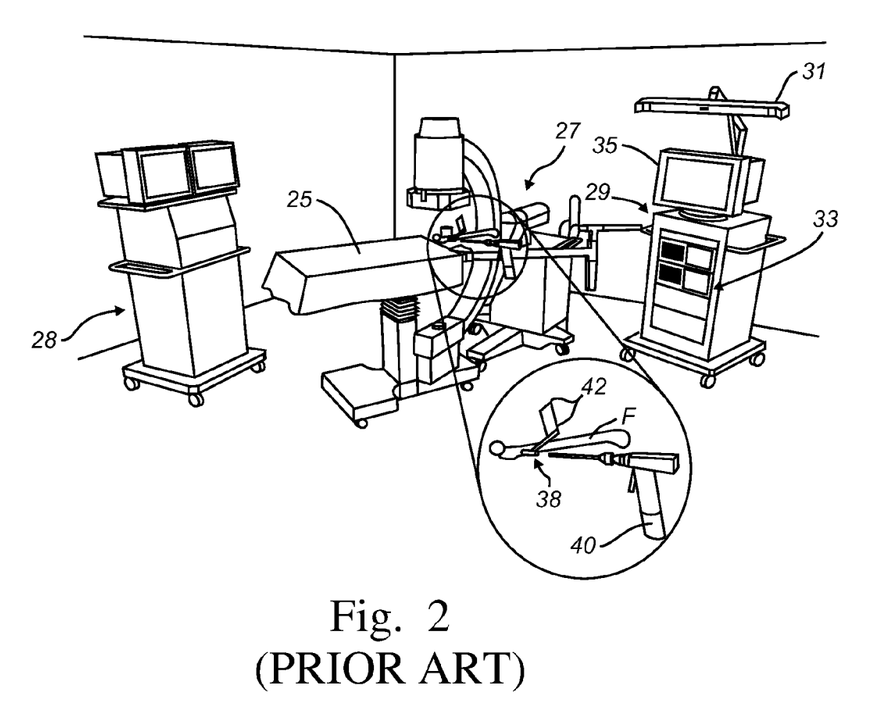
FIG. 2 is a perspective view of an operating room utilizing imaging equipment for image guide surgery.

An example of an image guided surgery (IGS) system is shown in FIG. 2. An x-ray imaging apparatus 27 is situated adjacent the operating table 25 to provide an intraoperative view of the surgical site, in this case the femur F. An x-ray monitoring apparatus 28 provides means for viewing the x-ray scan as the femur is being prepared to receive an implant, for instance. The IGS system also includes a localizer apparatus 29 that provides means for determining the position of elements in the surgical arena. The apparatus 29 includes a localizing device or sensor 31 that feeds information to a processor or computer 33 for display on a monitor 35. The localizing device 31 can take on a variety of forms, but all geared toward receiving signals from an emitter or position tracking element associated with a part of the patient, such as femur, or a surgical component, such as a drill guide 38. For instance, the localizing device 31 can constitute part of a visible light, IR, electromagnetic or RF triangulation system capable of fixing a position in space. Triangulation data from the localizing device 31 is fed to software within the processor that can calculate position information and generate a visual image on the display 35. Further details of suitable IGS systems can be found in U.S. Pat. No. 6,697,664, the disclosure of which is incorporated herein by reference.

As the disclosure of the '664 patent reveals, the typical image guided surgery system is complex and requires a great deal of equipment to provide real-time simulation and graphic display of the surgical site. What is needed is a system that allows for accurate bone resection or placement of surgical components without the expense and complexity of prior IGS systems.

SUMMARY OF THE INVENTION

In order to address this need, the present invention focuses on accurate placement of pins or screws into an object bone. The pins can then be used to position a standard cutting guide with the confidence that the bone resection conducted using the guide will be optimum. In order to accomplish this accurate pin placement, the present invention utilizes image guides surgical techniques, and particularly the use of a localizing sensor and position tracking elements associated with a surgical tool. In one embodiment of the invention, the surgical tool is a powered tool for placing a locating or support pin into a bone. The tool is outfitted with a position tracking element that can be sensed by the localizing sensor to determine the position of the tool in three-dimensional space. Similarly, the bone itself is provided with a position tracking element, at least initially, that will establish the spatial position of the bone.

A processor is linked to the localizing device or sensor to receive the data generated by the sensor. Software within the processor allows use selection of the proper location and attitude of the pin placement relative to the position tracking element associated with the bone. This position can be established using a pointer or other alignment device that is also provided with a position tracking device. The processor software can then calculate a relative difference between the spatial position of the bone and the spatial position of the proper pin location. Alternatively, if the bone is rigidly held so that it cannot move during the procedure, then only the spatial position of the pointer need be established.

Once the proper spatial location for the pin placement is determined, the surgeon manipulates the tool and its position data is sensed by the localizing device. The localizing device feeds this position information in real-time to the processor which compares the tool position to the proper location for the pin placement. In one embodiment of the invention, an annunciator provides a sensible signal to the surgeon to at least identify when the alignment of the tool matches the proper pin placement spatial position. The annunciator can provide an audible signal indicative of the relative spatial position. For instance, the audible signal can be generated only when the tool and pin placement spatial data coincide. Alternatively, the software can calculate a "closeness" value indicative of how close the tool is to its proper position, and then the audible annunciator can modulate the audible signal in relation to that "closeness" value.

In another embodiment, the annunciator is a visual indicator. The visual indicator can range from a light that illuminates when the spatial positions coincide to a series of lights that signal "closeness" and coincidence. The visual indicator can also constitute an image on a display associated with the processor that signifies the position of the tool relative to the proper pin placement position.

In a further embodiment of the invention, the tool itself is linked to the processor. The tool can be controlled automatically by the processor in relation to the spatial information evaluated by the processor software. In a specific embodiment, the tool is automatically activated when its spatial position coincides with the proper pin placement position. Where the tool is a pin driving tool, the tool is activated to drive the pin into the bone. Where the tool is a drill for driving a screw into the bone, the drill can be activated when it is properly positioned. As a further alternative, the drill can be constantly running but is configured to prevent the drill bit from engaging the bone unless and until the tool is properly positioned. In a specific embodiment, the drill is outfitted with a sheath that covers the rotating drill bit as the tool traverses the surface of the bone. Once the drill reaches its correct location, the sheath retracts, allowing the drill to be advanced into the bone.

In another aspect of the invention, a guide apparatus is provided that facilitates accurate placement of a guide or support pin into a bone. In one embodiment, the guide apparatus comprises a mounting body that is fastened to the bone in the proximity of a pre-determined guide pin location. A guide arm supports a position adjustment assembly over the guide pin location. The position adjustment assembly permits gross and fine adjustments of a pin guide. In this preferred embodiment of the invention, the pin guide is provided with a position tracking element that works through a localizing device or sensor to interactively evaluate the spatial position of the pin guide relative to the pre-determined guide pin location. Once the pin guide has been manipulated into coincidence with the pre-determined position, the surgeon can use the guide to drive a support pin into the bone.

Once the first pin has been properly position within the bone, a second pin can be introduced using the same guide apparatus. Alternatively, a cutting block can be mounted over the single support pin and then rotated into its proper alignment. The cutting block in this alternative embodiment is provided with its own position tracking element so that its spatial orientation can be evaluated in real-time. When the cutting block has been rotated into position, the cutting block itself is used as a pin guide for driving the second support pin into the bone.

It is one object of the present invention to provide systems and methods to facilitate making accurate cuts or resections of bone at a surgical site. It is a further object of the invention to utilize known image guide surgical techniques, while avoiding the high cost and complexity of such systems.

One benefit of the present invention is that it allows an orthopaedic surgeon to use conventional cutting blocks to perform bone resection procedures. Another benefit of the invention is that it can be used for a variety of functions in the orthopaedic arena, ranging from placing support pins for resection cutting blocks to accurate positioning of bone screws or pins. Other objects and benefits of the invention will become apparent upon consideration of the following written description taken together with the accompanying figures

DESCRIPTION OF THE FIGURES

FIGS. 9(*a*)-(*c*) are representations of sequential steps for positioning a cutting block using the present invention.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention provides systems and methods that utilize image guided surgical techniques and systems. More particularly, the invention utilizes a localizing device, such as the localizing sensor 31 shown in FIG. 2, and position tracking elements, such as the element 42, that cooperate with the localizing device to establish the spatial position of a component. A processor, like the processor 33 in FIG. 2, receives data from the localizing device and calculates the "global" or spatial position of the component. The invention can be implemented with a variety of localizing devices, position tracking elements and software used to determine spatial positions, including known devices and systems such as those described in U.S. Pat. No. 6,697,664 described above. The nature of the localizing device and tracking elements depends upon the type of signal being transmitted, which in turn may be governed by cost, line of sight limitations and the potential for interference with other equipment used in the operating room. For the purposes of the following description, it is contemplated that the position tracking elements emit an infrared (IR) signal and the localizing device includes an array of IR receivers.

Figure 3:
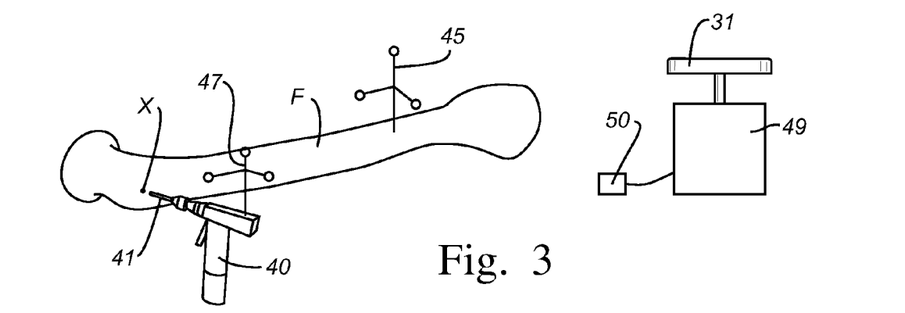
FIG. 3 is a perspective view of a system for accurate pin placement in a femur, in accordance with one embodiment of the present invention.
Figure 4:
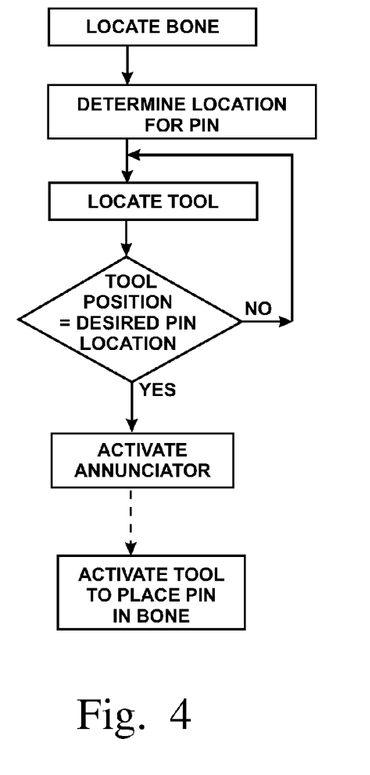
FIG. 4 is a flowchart of software steps performed by a processor in accordance with the present invention.

One embodiment of the present invention is depicted in FIGS. 3 and 4. In this illustration, the goal is to position a bone engaging element or support pin at a particular location X in a bone, such as a femur F. In a first step of the procedure, as reflected in the flowchart of FIG. 4, the pin location X is spatially located relative to a localizing device 31. A position tracking element 45 can be associated with the femur F and the pin location X calibrated to the location of the tracking element on the bone. Alternatively, a locating pin carrying its own position tracking element can be used to locate the pin location X on the femur F and transmit that location data to the localizing device 31. Once the location data has been transmitted, the locating pin is removed. Using the former approach, the location X can be established even when the bone moves slightly. Using the latter approach relies upon holding the femur in position by restraining the bone against movement so that the stored information regarding the position X is not obsoleted. With either approach, a position processor 49 can determine spatial coordinates of the pin location X using known algorithms. The nature of the spatial coordinate calculation and the form of the coordinates are not critical provided the same type of data and calculations are performed for all position tracking elements.

Once the pre-determined pin location has been established, the surgeon can manipulate a driving tool 40 in the vicinity of the pin location X. In one feature of the invention, the driving tool includes a position tracking element 47 that transmits to the localizing device 31, as shown in FIG. 3. Thus, the spatial position of the tool 40 can be established in real-time. Preferably, the position tracking element 47 includes enough IR transmitters so that not only the spatial position but also the orientation of the tool can be determined. In other words, the object is to ascertain where the working end 41 of the tool is located relative to the femur F and to determine the alignment of the working end, since this alignment will determine whether the bone engaging element or pin is inserted at a proper angular orientation relative to the bone.

Returning to the flowchart in FIG. 4, once the pre-determined pin location has been established, software within the processor 49 evaluates the current position of the tool 40 using known techniques, and compares that current position to the spatial position of the pin location X. If the spatial coordinates of the tool do not match the spatial coordinates of the pin location X, the processor continues to receive position data. The degree of coincidence required to establish a spatial match can be pre-determined or calibrated to the size of pin and the criticality of the pin placement. For instance, an acceptable pin placement may be within a radius of about 1 mm and about 1 degree of the pre-determined pin location X without adversely affecting the ensuing orthopaedic procedure. Again, the processor can use known proximity tests to determine spatial coincidence or not.

Once these coordinates coincide, the processor activates an annunciator 50 (FIG. 3) that provides a sensible indication that the tool 40 is properly positioned. In one embodiment, the annunciator provides an audible signal, such as a beep, to indicate that the driving tool 40 is positioned over the location X. In a modification of this embodiment, the processor can be programmed to variably activate the audible annunciator. For instance, the annunciator 50 can emit a sound of one frequency as the tool is manipulated in search of the proper location, and then emit a sound of a different frequency and/or intensity when spatial coincidence is achieved. The modulation of the sound can be calibrated to the proximity of the working end 41 of the tool to the location X.

Once the annunciator signals spatial coincidence between the working end 41 and the location X, the tool 40 can be activated to place the fastener or pin into the femur F. Where the annunciator is sensed by the surgeon, the surgeon can operate the tool in a known manner. In an alternative, described in more detail herein, the processor 49 can direct the activation of the driving tool.

In certain embodiments of the invention, the annunciator provides a visual indication of spatial coincidence. In a specific embodiment, that visual indication can be projected on a display device, such as the monitor 35 of FIG. 2. This option is less desirable because it requires the surgeon to watch a monitor rather than the surgical site (at least in the absence of a heads-up display on a surgical visor). More desirably, the annunciator 50 can include one or more lights placed in a position that can be sensed by the surgeon without removing his/her concentration from the patient at hand. Like the audible annunciator described above, the visual annunciator can be activated only when spatial coincidence is achieved. Alternatively, the visual annunciator can modulate the light, such as by strobing the light, varying the color or sequentially activating an array of lights indicative of proximity to the location X and eventually spatial coincidence.

Figure 5:
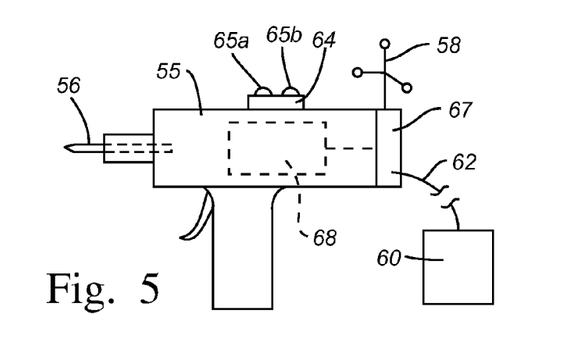
FIG. 5 is a side view of a driving tool in accordance with one aspect of the present invention.

In another embodiment of the invention, a pin driving tool 55 is configured to propel a pin 56 into bone. The tool can be a driving tool known for use in the orthopaedic field. The tool can be spring-loaded, electromagnetic, pneumatic or a combustion-type tool. The tool 55 includes a position tracking element 58, as described above to provide real-time data regarding the position and orientation of the tool relative to a pin implantation site on a bone. The tool 55 includes an on-board controller 67 that is connected via a communication link 62 to a master controller 60. The master controller 60 can be part of the processor 49 and operates to send signals to the on-board controller 67. The communication link 62 can be a wire connecting the two components or can be wireless, such as an RF transmission.

In one aspect of this embodiment, the annunciator 64 is associated with or mounted on the tool 55 in a position where it is readily visible to the surgeon. The tool 55 can include a plurality of LEDs 65a, 65b that are used to indicate closeness to and coincidence with the pin location. The annunciator is connected to the on-board controller 67 that responds to signals from the master controller 60 to activate the appropriate LED 65a, 65b. In a specific embodiment, one LED 65a can be activated as the surgeon searches for the proper pin location, while the other LED 65b can be activated once the pin 56 is situated over the pre-determined pin location.

In another embodiment of the present invention, the system contemplates automatically controlling the operation of the driving tool when its position coincides with the pre-determined pin position. The on-board controller 67 can also be connected to the motor 68 to activate the motor in response to a signal from the master controller 62. With this embodiment, the surgeon need not activate the tool in response to an annunciator signal. Automatic control thus facilitates the pin placement process.

Figure 6:
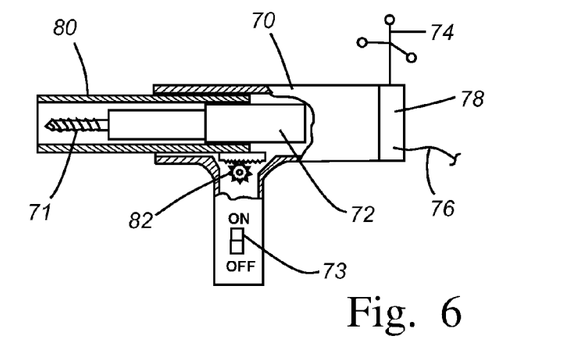
FIG. 6 is a side view of an alternative driving tool for use with the present invention.

This automatic control feature can also be implemented where the tool is a drill operable to prepare a bore in bone to receive a bone screw, for instance. Thus, as shown in FIG. 6, a drill 70 can include a tracking element 74 and an on-board controller 78. The on-board controller 78 communicates with the processor 49 and master controller 60 through a communication link 76. These components can be configured similar to the like components discussed above with respect to FIG. 5. Similarly, the on-board controller 78 can be connected to the motor 72 of the drill 70 to activate the drill at the appropriate time.

In a further alternative, it is contemplated that the drill 70 will be continuously running as the surgeon searches for the proper location to drill into the bone. In this instance, the present invention provides a mechanism for preventing access to the bone until spatial coincidence is achieved. In one specific embodiment, a sheath 80 is provided that encloses or covers the drill bit 71 as it is rotating. The sheath is connected to a retraction mechanism 82 that retracts or extends the sheath in response to a signal from the on-board controller 78. The retraction mechanism 82 can take on a variety of forms, such as the rack and pinion configuration depicted in FIG. 6. The mechanism 82 is preferably electrically operated and capable of rapid retraction of the sheath 80.

The drill 70 includes its own power switch 73 to provide the surgeon with absolute control over the activation of the drill. Thus, rather than rotating the drill bit 71 continuously during the procedure, the surgeon can elect to de-activate the drill until the bit is nearly aligned with the proper location. When the switch 73 is turned on, the on-board controller then takes charge of activating the motor 72 and/or retracting the sheath 80.

In an alternative approach, the bit 71 itself can be retracted into the body of the tool 70. With this approach, the retraction mechanism 82 can be engaged to the drill motor 72 and operate to move the motor back into the body of the tool with the bit 71 engaged thereto. In yet another alternative, the cutting edges of the drill bit 71 can be configured to be withdrawn as the bit is rotating, and then extended when a drilling operation is to be performed.

With the approaches of FIGS. 3-6, the invention provided means for gauging the spatial position of the working tool, such as the pin gun 55 or drill 70. These embodiments utilize annunciators to signify alignment of the working end of the tool with the pre-determined location on the bone. In certain variations, an on-board controller automatically controls the operation of the tool in response to an indication of spatial alignment.

Figure 7:
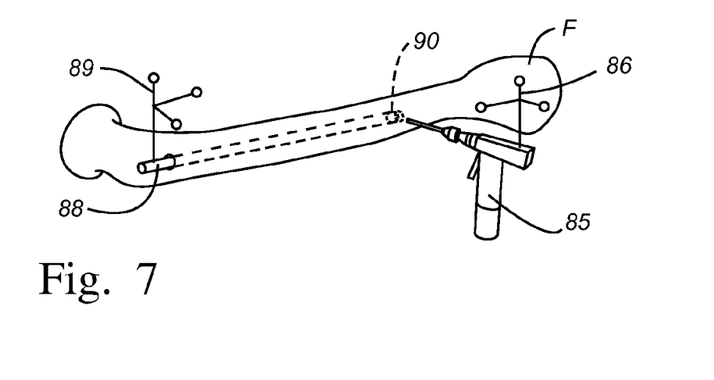
FIG. 7 is a perspective view of a system for placing a pin through a opening in a femoral nail using the present invention.

These same aspects of the present invention can be used to drill into a bone at a predetermined position. For instance, as shown in FIG. 7, an intramedullary nail 88, disposed within the medullary canal of a bone F, includes an opening 90 therethrough. In certain orthopaedic procedures, it is necessary to extend a fastener or bone engaging element through the opening 90 in situ. In this instance, a position tracking element 89 can be associated with the intramedullary nail 88, the bone F or the opening 90 itself. The processor 49 evaluates the data transmitted by the tracking element 89 to determine the position of the opening 90. The working tool 85, which is typically a drill, is also provided with a position tracking element 86. The real-time position of the drill 85 is assessed by the processor as described above. When the spatial position of the working end of the drill coincides with the pre-determined position of the opening 90, any one of the protocols described above can be implemented—i.e., an annunciator can be activated to prompt the surgeon to operate the drill at that location, or the drill can be automatically controlled.

Figures 8, 9:
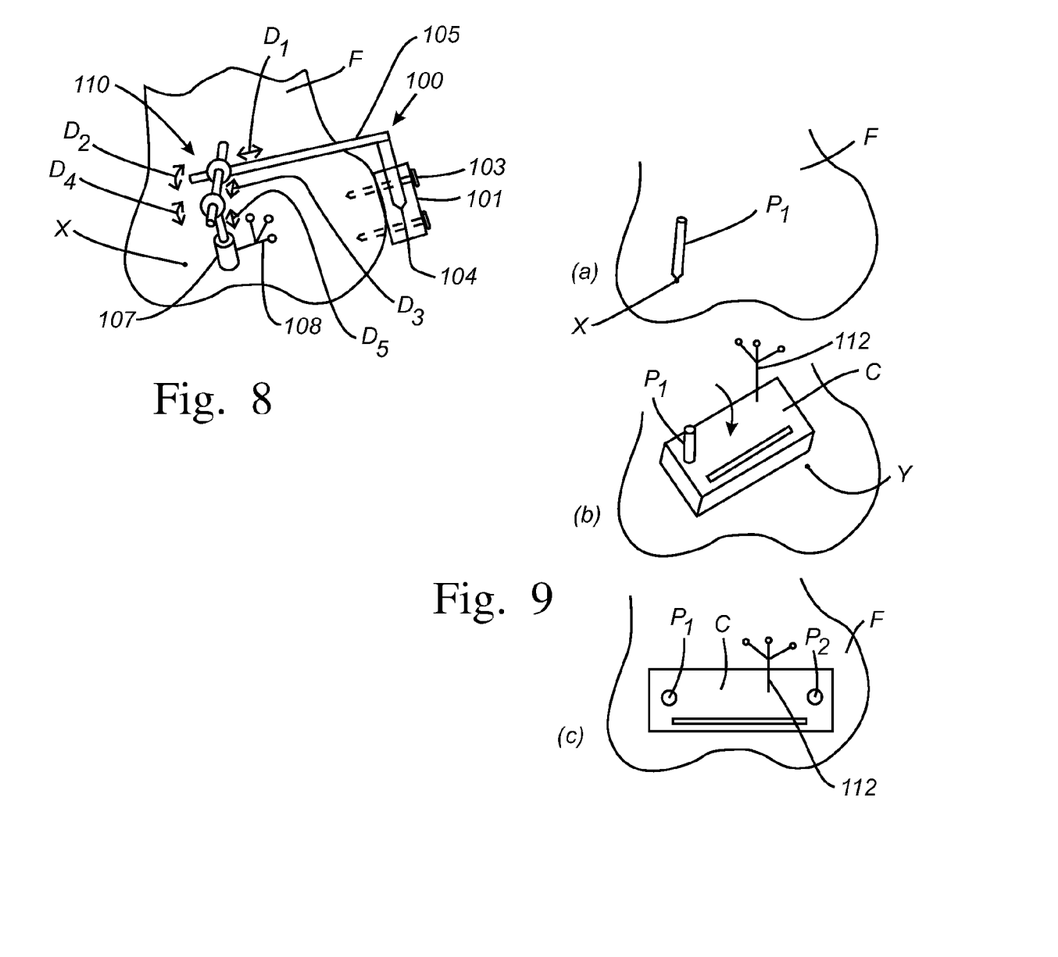
FIG. 8 is a perspective view of a guide apparatus in accordance with a further embodiment of the invention for positioning a pin in a bone.

In a further approach of the present invention, a pin guide, rather than the pin itself, is navigated into position using the image guides surgical techniques described above. In this embodiment, a guide apparatus 10 includes a body 101 mounted to a bone F by mounting pins 103, as shown in FIG. 8. The location of the mounting body is not critical, but is preferably near the pre-determined location X for the placement of a pin used to support a standard cutting block (such as the cutting block C shown in FIG. 9(*b*)). The guide apparatus includes a guide arm 105 supported by the block 101 and configured to extend across the bone F toward the pin location X. The guide arm can be pivotably mounted within a bore 104 defined in the mounting block 101 or can be rigidly fixed to the block. If the guide arm 105 is pivotably mounted, it is preferably mounted within a bushing that adds frictional resistance to pivoting of the guide arm to prevent unnecessary movement of the arm. The pivot mount can also include a clamp to fix the guide arm 105 to the mounting block 101 when the arm has been pivoted to its preferred position.

The guide arm 105 supports a position adjustment assembly 110 that is configured to align a pin guide 107 with the pre-determined location X. The pin guide 107 is outfitted with a tracking element 108, which can be similar to the tracking elements discussed above. The tracking element is used in conjunction with a localizing device, such as the device 31 described above, for a real-time determination of the spatial location of the pin guide 107 relative to the pin location X, the spatial coordinates of which have been determined beforehand. The relative position between these two points is calculated in the manner described above to determine whether the pin guide spatially coincides with the pin location. In the prior embodiments, the working tool was manually manipulated by the surgeon as the position of the tool was sensed in real-time. With the embodiment of FIG. 8, the "working tool" is the pin guide and its position is controlled indirectly by manipulation of the position adjustment assembly 110.

With this embodiment, the ultimate goal is to accurately position a standard cutting guide, such as the guide C shown in FIG. 9(*b*), relative to a bone, such as the femur. The guide apparatus 100 is manipulated until the pin guide 107 coincides with the pre-determined pin location X (FIGS. 8 and 9(*a*)). When the pin guide is properly aligned, the surgeon can use the guide to drive a support pin $P_1$ into the bone. In one approach, the guide apparatus is used to place a second support pin $P_2$ as shown in FIG. 9(*c*), and the cutting block C is mounted on the pins.

In an alternative approach, the first pin $P_1$ is positioned using the guide apparatus 100. The guide apparatus is then removed from the bone F. The cutting block C can be provided with a position tracking element 112 that sends signals to a localizing device in the manner described above. The position of the cutting block C can then be compared to a predetermined position value associated with either the cutting block or with the second support pin $P_2$. In the latter case, the cutting block C is acting as like the pin guide 107 in that it is being positioned to align with a second pin location Y (FIG. 9(*b*)) and is used to guide a pin driven into the bone F by the surgeon.

When the first pin P1 is placed within the bone, the cutting block C is mounted on that pin, as shown in FIG. 9(*b*). The cutting block is then rotated about the first pin until its position coincides with the proper position for the second pin $P_2$. This position is verified using information transmitted by the position tracking element 112, read by the localizing device 31 and deciphered by the processor 49 (see FIG. 3). At that point, the second support pin $P_2$ can be driven into the bone F using the cutting block as a pin guide.

It can be appreciated that this embodiment of the invention accommodates a simple standard cutting block. Since the location of the mounting pins $P_1$ and $P_2$ is accurately navigated, there is not need for the cutting block to include any gross or fine adjustment capabilities. Of course, differently sized cutting blocks may be required for differently sized bones. This size difference can be accounted for in establishing the pre-determined pin placement locations X and Y.

Figure 10:
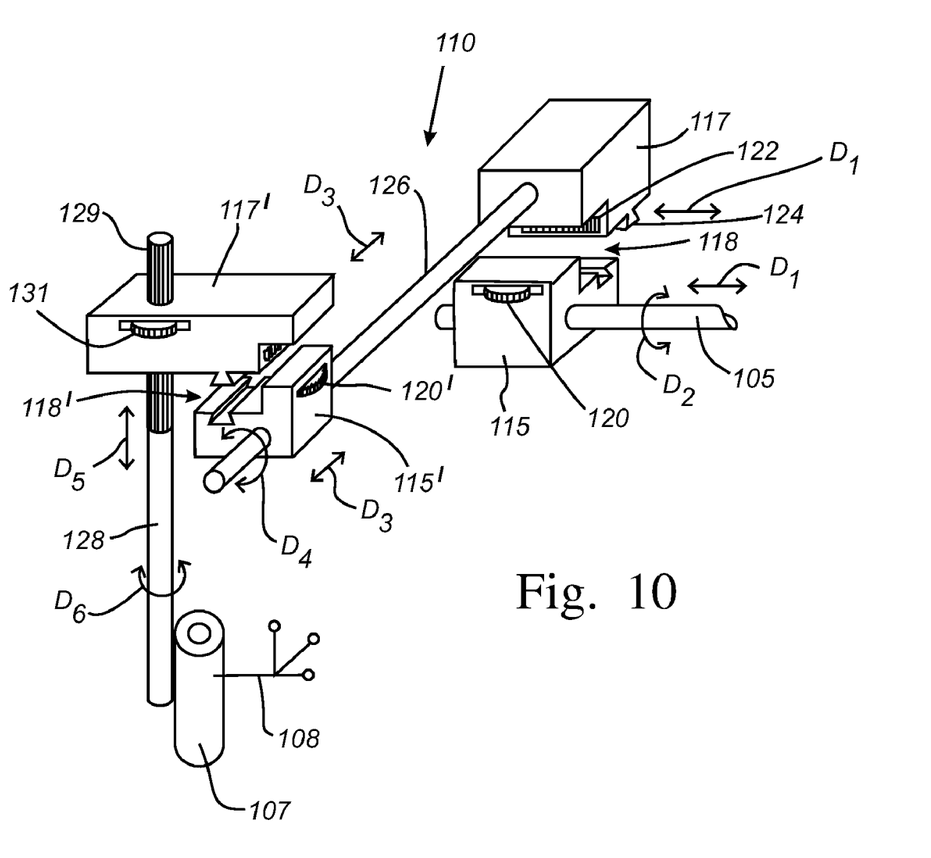
FIG. 10 is an enlarged exploded perspective view of the guide apparatus shown in FIG. 8.

The details of one specific embodiment of the position adjustment assembly 110 are shown in FIG. 10. This assembly permits gross and fine adjustments to the position of the pin guide 107. It is understood that this adjustment assembly can work in conjunction with the annunciators 50 or 64 described above. In particular, an annunciator can signify coincidence between the position of the pin guide 107 and the pre-determined pin location(s) $P_1$ (and $P_2$). When the annunciator is activated, the surgeon stops making adjustments with the position adjustment assembly 110.

In one embodiment of the invention, the position adjustment assembly 110 includes a gross positioning block 115 that is slidably mounted on the guide arm 105, as shown in FIG. 10. The gross positioning block 115 can translate or rotate along the guide arm 105 in the degrees of freedom $D_1$ and $D_2$, as indicated by the directional arrows in FIG. 10. Preferably the block 115 includes a friction bushing (not shown) to increase the static and sliding friction between the block and the guide arm. The block 115 can also incorporate a clamp (not shown) for fixing the position of the block relative to the guide arm once a gross position of the block has been established.

The gross positioning block 115 supports a fine adjustment block 117 with a fine adjustment mechanism 118 disposed therebetween. The fine adjustment block 117 supports a support arm 126 at an angle relative to the guide arm 105. Preferably, the support arm 126 is situated at a right angle to the guide arm, as depicted in FIG. 10. The support arm 126 is preferably fixed within the fine positioning block 115.

The fine adjustment mechanism 118 is configured to permit small changes in the position of the fine positioning block 117 relative to the gross positioning block 115. In other words, the fine adjustment mechanism 118 permits small adjustments in the spatial position of the pin guide 107 in the translational degree of freedom $D_1$ (see also FIG. 8). The fine adjustment mechanism 118 can assume a variety of forms capable of producing minute changes in relative position, preferably on the order of 0.1-0.5 mm. In a specific embodiment, the mechanism 118 can include a thumbwheel gear 120 rotatably mounted within the gross positioning block 115 and a mating rack gear 122 mounted within the fine positioning block 117. A dovetail mount 124 can be provided between the two blocks 115, 117 to slidably support the fine positioning block on the gross positioning block and maintain the two gears 120 and 122 in contact. The thumbwheel gear can be mounted within the block 115 so that a portion of the gear 120 is accessible to be manually rotated by the surgeon to make fine positional adjustments in the degree of freedom $D_1$.

As explained above, a support arm 126 projects from the fine positioning block 117. A second gross positioning block 115' is slidably mounted on the support arm 126 in the same manner as the block mounted on the guide arm 105. A second fine positioning block 117' and a second fine adjustment mechanism 118' can be provided to permit fine adjustments in the translational degree of freedom $D_3$. The gross and fine positioning adjustment capabilities in the degrees of freedom $D_3$ and $D_4$ relative to the support arm 126 can be the same as the adjustments accomplished relative to the guide arm 105 described above.

The fine adjustment block 117' supports a vertical support arm 128 to which the pin guide 107 is mounted. The vertical support arm can be slidably mounted within the block 117' for translation in the degree of freedom $D_5$ and rotation in the degree of freedom $D_6$. Again, the mount between the block 117' and the vertical support arm 128 can include a friction bushing to control the movement of the arm relative to the block. Alternatively, the vertical support arm 128 can include splines 129 at its free end. The fine positioning block 117' can include a thumbwheel gear 131 that meshes with the splines 129 to permit fine rotational adjustments of the arm 128 in the degree of freedom $D_6$. The splines 129 allow the arm 128 to translate vertically relative to the thumbwheel gear 131 without disturbing the fine rotational adjustment capability. Fine adjustment in the vertical translational degree of freedom $D_5$ is typically not required because the pin guide 107 can be moved into direct contact with the bone F once the positional adjustments have been made in the other degrees of freedom. The fine rotational adjustment capability provided by the splines 129 and thumbwheel gear 131 can be implemented in the gross positioning blocks 115 and 115' to accommodate fine rotational adjustments in the degrees of freedom $D_2$ and $D_4$.

In using the guide apparatus 100 of the present embodiment, the gross position of the pin guide 107 can be established relative to bony landmarks on the bone F. The fine adjustment thumbwheel gears 120, 120' and 131 can be manipulated as the real-time spatial position of the pin guide 107 is reported using the position tracking element 108. When the spatial position of the pin guide coincides with the pre-determined pin location(s) X (or Y), the pin guide can be moved into contact with the bone and the surgeon can drive a pin $P_1$ (or $P_2$) into the bone using a standard driving tool.

The systems and methods of the present invention are not limited to the pin placement or drilling operation s described above, or to any particular location in the body. For instance, the bone being prepared can be anywhere in the skeletal structure, such as the shoulder, elbow, hip, ankle, spine and cranium. The approach described in connection with FIGS. 9(a)-(c) can be used for guide placement of a bone plate, instead of the cutting guide shown the figures. For instance, in some orthopaedic procedures, a bone plate is fastened to a bone spanning a fracture. Accurate placement of the plate and associated bone fasteners can be facilitated with the present invention.

The invention is particularly suited for precision bone working operations. Thus, the invention is not limited to pin placement or drilling into bone, but can include other operations, such as cutting, burring, polishing, grinding, rasping, or other similar operations. For instance, in one alternative procedure, it is necessary to prepare the distal end of the femur to receive an femoral implant. This preparation can require shaving, burring and polishing the distal end of the femur using an appropriate tool. The tool would carry the position locating device 47 described above so that the working end of the tool can be established in real-time. The tool can be activated as described above when it aligns with an array of stored locations or falls within a range of pre-determined locations on the bone. Thus, in the case of a burring tool, the surgeon can move the tool across the distal end of the femur while the tool spatial position is determined by the processor 49. When the burring tool is at a location that has been previously determined to require finishing, the surgeon can be prompted to activate the tool by an annunciator 50, or the tool can be automatically activated in the manners described above. Other tools can be similarly manipulated using the techniques and systems of the present invention.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A system for accurately guiding placement of a bone engaging element in a bone comprising:
   a guide configured to guide movement of the bone engaging element toward a location on a bone, said guide having a bore through which said bone engaging element may be advanced, and said bore defining a first longitudinal axis; and
   a support apparatus configured to support said guide, said support apparatus including;
      a support body mountable to the bone;
      an arm extending from said support body; and
      a position adjustment assembly supported on said arm, said position adjustment assembly including (i) a first gross adjustment mechanism configured to permit gross adjustment of said guide in relation to said, support body along a second longitudinal axis, (ii) a first fine adjustment mechanism configured to permit fine adjustment of said guide in relation to said support body along said second longitudinal axis, (iii) a second gross adjustment mechanism configured to permit gross adjustment of said guide in relation to said support body along a third longitudinal axis, (iv) a second fine adjustment mechanism configured to permit fine adjustment of said guide in relation to said support body along said third longitudinal axis, and (v) a third adjustment mechanism configured to permit adjustment of said guide in relation to said support body along said first longitudinal axis,
      wherein said first longitudinal axis is not coincident with said second longitudinal axis,
      wherein said first longitudinal axis is not coincident with said third longitudinal axis, and
      wherein said second longitudinal axis is not coincident with said third longitudinal axis.

2. The system of claim 1, wherein said guide is a pin guide and the bone engaging element is a pin configured to be placed in bone.

3. The system of claim 1, wherein said position adjustment assembly includes:
   a first positioning block movably mounted on said arm; and
   a second positioning block movably supported on said first positioning block.

4. The system of claim 3, wherein:
   one of said first positioning block and said second positioning block includes a dovetailed recess, and
   the other of said first positioning block and said second positioning block includes a dovetailed member positioned within said dovetailed recess.

5. The system of claim 3, wherein said position adjustment assembly further includes:
   a first support member extending from said second positioning block;
   a third positioning block movably mounted on said first support member; and
   a fourth block movably supported on said third positioning block.

6. The system of claim 5, wherein said position adjustment assembly includes a second support member connected to said fourth positioning block, and wherein said guide is connected to said second support member.

7. The system of claim 1, wherein said first fine adjustment mechanism includes:
   a rack gear mounted to one of said first positioning block and said second, positioning block; and
   a thumbwheel gear configured to mesh with said rack gear and mounted to the other of said first positioning block and said second positioning block.

8. A guide assembly for a bone engaging element, comprising:
   a guide configured to guide movement of the bone engaging element, said guide having a bore through which said bone engaging element may be advanced, and said bore defining a first longitudinal axis; and
   a support apparatus configured to support said guide, said support apparatus including;
      a body mountable to a bone;
      a first support member extending from said body; and
      a position adjustment assembly supported on said first support member, said position adjustment assembly including (i) a first gross adjustment mechanism configured to permit gross adjustment of said guide in relation to said body along a second longitudinal axis, (ii) a first fine adjustment mechanism configured to permit fine adjustment of said guide in relation to said body along said second longitudinal axis, (iii) a second gross adjustment mechanism configured to permit gross adjustment of said guide in relation to said body along a third longitudinal axis, (iv) a second fine adjustment mechanism configured to permit fine adjustment of said guide in relation to said body along said third longitudinal axis, and (v) a third adjustment mechanism configured to permit adjustment of said guide in relation to said body along said first longitudinal axis,
      wherein said first longitudinal axis is not coincident with said second longitudinal axis,
      wherein said first longitudinal axis is not coincident with said third longitudinal axis, and
      wherein said second longitudinal axis is not coincident with said third longitudinal axis.

9. The system of claim 8, wherein said position adjustment assembly includes:
   a first positioning block movably mounted on said first support member; and
   a second positioning block movably supported on said first positioning block.

10. The system of claim 9, wherein said position adjustment assembly further includes:
    a second support member extending from said second positioning block;
    a third positioning block movably mounted on said second support member; and
    a fourth block movably supported on said third positioning block.

11. The system of claim 10, wherein:
    said position adjustment assembly further includes a third support member connected to said fourth positioning block, and
    said guide is connected to said third support member.

12. The system of claim 10, wherein:
    one of said first positioning block and said second positioning block includes a first dovetailed recess, and
    the other of said first positioning block and said second positioning block includes a first dovetailed member positioned within said first dovetailed recess.

13. The system of claim 12, wherein:
    one of said third positioning block and said fourth positioning block includes a second dovetailed recess, and
    the other of said third positioning block and said fourth positioning block includes a second dovetailed member positioned within said second dovetailed recess.

14. The system of claim 8, wherein said first fine adjustment mechanism includes:
- a first rack gear mounted to one of said first positioning block and said second positioning block; and
- a first thumbwheel gear configured to mesh with said first rack gear and mounted to the other of said first positioning block and said second positioning block.

15. The system of claim 14, wherein said second fine adjustment mechanism includes:
- a second rack gear mounted to one of said third positioning block and said fourth positioning block; and
- a second thumbwheel gear configured to mesh with said second rack gear and mounted to the other of said third positioning block and said fourth positioning block.

16. A guide assembly for a bone engaging element, comprising:
- a guide configured to guide movement of the bone engaging element along a first longitudinal axis; and
- a support apparatus configured to support said guide, said support apparatus including;
  - a body mountable to a bone;
  - a first support member extending from said body; and
  - a position adjustment assembly supported on said first support member, said position adjustment assembly including (i) a first gross adjustment mechanism configured to permit gross adjustment of said guide in relation to said body along a second longitudinal axis, (ii) a first fine adjustment mechanism configured to permit fine adjustment of said guide in relation to said body along said second longitudinal axis, (iii) a second gross adjustment mechanism configured to permit gross adjustment of said guide in relation to said body along a third longitudinal axis, (iv) a second fine adjustment mechanism configured to permit fine adjustment of said guide in relation to said body along said third longitudinal axis, and (v) a third adjustment mechanism configured to permit adjustment of said guide in relation to said body along said first longitudinal axis,
- wherein said first longitudinal axis is not coincident with said second longitudinal axis,
- wherein said first longitudinal axis is not coincident with said third longitudinal axis, and
- wherein said second longitudinal axis is not coincident with said third longitudinal axis.

17. The system of claim 16, wherein said position adjustment assembly includes:
- a first positioning block movably mounted on said first support member;
- a second positioning block movably supported on said first positioning block;
- a second support member extending from said second positioning block;
- a third positioning block movably mounted on said second support member; and
- a fourth block movably supported on said third positioning block.

18. The system of claim 17, wherein:
- said position adjustment assembly further includes a third support member connected to said fourth positioning block, and
- said guide is connected to said third support member.

19. The system of claim 18, wherein:
- said first fine adjustment mechanism includes (i) a first rack gear mounted to one of said first positioning block and said second positioning block, and (ii) a first thumbwheel gear configured to mesh with said first rack gear and mounted to the other of said first positioning block and said second positioning block, and
- said second fine adjustment mechanism includes (i) a second rack gear mounted to one of said third positioning block and said fourth positioning block, and (ii) a second thumbwheel gear configured to mesh with said second rack gear and mounted to the other of said third positioning block and said fourth positioning block.

20. The system of claim 19, wherein:
- one of said first positioning block and said second positioning block includes a first dovetailed recess,
- the other of said first positioning block and said second positioning block includes a first dovetailed member positioned within said first dovetailed recess,
- one of said third positioning block and said fourth positioning block includes a second dovetailed recess, and
- the other of said third positioning block and said fourth positioning block includes a second dovetailed member positioned within said second dovetailed recess.

* * * * *